United States Patent
Guazzi et al.

(10) Patent No.: US 10,993,676 B2
(45) Date of Patent: May 4, 2021

(54) SIGNAL PROCESSING METHOD AND APPARATUS

(71) Applicant: OXFORD UNIVERSITY INNOVATION LIMITED, Oxford (GB)

(72) Inventors: Alessandro Guazzi, Oxford (GB); Syed Ahmar Shah, Oxford (GB); Lionel Tarassenko, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 446 days.

(21) Appl. No.: 15/533,892

(22) PCT Filed: Dec. 8, 2015

(86) PCT No.: PCT/GB2015/053755
§ 371 (c)(1),
(2) Date: Jun. 7, 2017

(87) PCT Pub. No.: WO2016/092291
PCT Pub. Date: Jun. 16, 2016

(65) Prior Publication Data
US 2017/0332978 A1 Nov. 23, 2017

(30) Foreign Application Priority Data
Dec. 8, 2014 (GB) ................................ 1421786

(51) Int. Cl.
*A61B 5/00* (2006.01)
*A61B 5/08* (2006.01)
(Continued)

(52) U.S. Cl.
CPC ........ *A61B 5/7278* (2013.01); *A61B 5/02416* (2013.01); *A61B 5/0816* (2013.01);
(Continued)

(58) Field of Classification Search
CPC ... A61B 5/7278; A61B 5/7246; A61B 5/7257; A61B 5/0836; A61B 5/0816; G01R 23/167
See application file for complete search history.

(56) References Cited

U.S. PATENT DOCUMENTS 3,656,097 A  4/1972 Massa
4,037,151 A  7/1977 Takeuchi
(Continued)

FOREIGN PATENT DOCUMENTS

WO  WO-13027027 A2  2/2013
WO  WO-2014031082 A1  2/2014

OTHER PUBLICATIONS

International Search Report and Written Opinion of the International Searching Authority issued in PCT/GB2015/053755, dated Feb. 22, 2016. ISA/EPO.
(Continued)

*Primary Examiner* — Regis J Betsch
*Assistant Examiner* — Jeremy A Delozier
(74) *Attorney, Agent, or Firm* — Harness, Dickey & Pierce, P.L.C.

(57) ABSTRACT

A method and apparatus for estimating the frequency of a dominant periodic component in an input signal by modelling the input signal using auto-regressive models of several different orders to generate candidate frequencies for the periodic component, generating synthetic sinusoidal signals of each of the candidate frequencies, and calculating the cross-correlation of the synthetic signals with the original signal. The frequency of whichever of the synthetic signals has the highest cross-correlation with the original signal is taken as the estimate of the frequency for the dominant periodic component of the input signal. The method may be applied to any noisy signal which has a suspected periodic component, for example physiological signals such as photoplethysmogram signals, and in the estimation of heart rate and breathing rate from such physiological signals.

22 Claims, 3 Drawing Sheets

(51) Int. Cl.
    *A61B 5/1455*     (2006.01)
    *A61B 5/083*     (2006.01)
    *A61B 5/024*     (2006.01)
    *G01R 23/167*     (2006.01)

(52) U.S. Cl.
    CPC ........ *A61B 5/0836* (2013.01); *A61B 5/14551* (2013.01); *A61B 5/7214* (2013.01); *A61B 5/7246* (2013.01); *A61B 5/7253* (2013.01); *A61B 5/7257* (2013.01); *G01R 23/167* (2013.01); *A61B 2576/00* (2013.01)

(56) References Cited

U.S. PATENT DOCUMENTS

| | | |
|---|---|---|
| 4,291,269 A | 9/1981 | Nossen |
| 2004/0122317 A1* | 6/2004 | Heim ................ G06F 17/141 600/437 |
| 2010/0298730 A1* | 11/2010 | Tarassenko .......... A61B 5/0816 600/529 |
| 2011/0151817 A1 | 6/2011 | Swarts et al. |
| 2014/0073956 A1 | 3/2014 | Engelbrecht et al. |
| 2015/0208931 A1* | 7/2015 | Kasamsook ......... A61B 5/7246 600/479 |
| 2016/0361021 A1* | 12/2016 | Salehizadeh ......... A61B 5/0245 |
| 2017/0347967 A1* | 12/2017 | Guazzi ................ A61B 5/6898 |

OTHER PUBLICATIONS

GB Search Report of the Intellectual Property Office under Section 17 issued in application No. GB1421786.3, dated May 14, 2015.

Kamshilin, Alexei A., et al: "Photoplethysmograohic imaging of high spatial resolution", Biomedical Optics Express, vol. 2, No. 4, Apr. 1, 2011 (Apr. 1, 2011), pp. 996-1006.

Karlen, Walter et al., "Multiparameter Respiratory Rate Estimation From the Photoplethysmogram", IEEE Transactions on Biomedical Engineering, vol. 60, No. 7, Jul. 2013.

* cited by examiner

SIGNAL PROCESSING METHOD AND APPARATUS

CROSS REFERENCE TO RELATED APPLICATIONS

This application is a U.S. National Phase Application under 35 U.S.C. 371 of International Application No. PCT/GB2015/053755 filed on Dec. 8, 2015 and published as WO 2016/092291 A1 on Jun. 16, 2016. This application is based on and claims the benefit of priority from Great Britain Patent Application No. 1421786.3 filed Dec. 8, 2014. The entire disclosures of all of the above applications are incorporated herein by reference.

The present invention relates to the processing of signals, especially noisy signals, to determine the frequency of periodic components thereof.

A common technique in signal processing is spectral analysis, that is to say examining the frequency content of a signal. For example there may be a desire to detect one or more periodic components of a noisy signal and to produce estimates of the frequency and possibly amplitude of those components. There are many standard techniques for spectral analysis, such as the Fast Fourier Transform or the use of auto-regressive (AR) models and different techniques are used in different circumstances depending on the nature of the signal and the result required.

The use of auto-regressive (AR) models for frequency estimation has many advantages over other spectral analysis techniques. It can provide a significantly higher frequency resolution than, for example, the Fast Fourier Transform and it can cope well with noisy input signals. Auto-regressive (AR) modelling has been used extensively in speech analysis, but more recently the use of auto-regressive modelling for analysing signals from physiological sensors has been proposed. For example the use of AR modelling for spectral analysis of a photoplethysmographic (PPG) input signal from an oxygen saturation finger probe is described in US-A1-2010/0298730. The use of auto-regressive modelling in the analysis of PPGi signals from a video camera is disclosed in WO-A2-2013/027027. In both cases AR modelling is used to estimate the frequency of periodic physiological components in the input PPG signal so that the value of the heart rate or breathing rate (or both) can be estimated.

The basic assumption underlying AR modelling is that a new data point can be predicted by using a weighted sum of the previous N data points. The choice of N also known as the model order, is critical in determining how well a given model will fit the time-series. In practice, though, a single model order will not necessarily fit optimally to a whole input signal. One reason for this is that in a noisy signal, the noise varies and at different times different model orders may fit better. For this reason when using AR modelling to analyse noisy signals it has been proposed, as in the two patent applications mentioned above, to fit multiple models of different order to the input signal and at any time to select the model order and dominant pole from that model order in some way.

Several methods have been proposed to determine the optimal model order. One of the most common methods is Akaike's information criterion, which minimises the prediction variance error associated with each model order and penalises higher model orders. This is described in, for example, Ritei Shibata, "Selection of the Order of an Autoregressive Model by Akaike's Information Criterion", Biometrika, Vol 63., No. 1, April 1976. The drawback with this approach is that the result depends heavily on the size of the penalty term chosen.

Once an AR model has been fitted to the data, the spectral properties of the model may be visualised by treating the model as a noise-shaping filter. By transforming the AR model's difference equation into the z-domain, its transfer function may be found. Using the substitution $z=\exp(j\omega T)$ where $\omega=2\pi f$ and T is the sampling period, the spectral properties of the modelled time series can be derived from the angle and magnitude of the poles that characterise the all-pole transfer function.

It is often difficult to find the correct model order, and the incorrect choice of model order will lead to incorrect estimates of the dominant frequency (corresponding to the heart rate or breathing rate, for example). In WO-A2-2013/027027 the frequencies represented by the dominant poles of the various models are averaged to provide an overall frequency estimate for each time window.

It would therefore be advantageous to improve the techniques for choosing the model order and the pole.

Accordingly the present invention provides a method of analysing an input signal to estimate the frequency of a periodic signal therein comprising the steps of: receiving the input signal; generating frequency domain candidates for the periodic signal; for each frequency domain candidate generating a synthetic signal of the same frequency; calculating in the time domain a measure of the similarity of each synthetic signal with the input signal; outputting as the estimate of the frequency of the periodic signal the frequency of the synthetic signal with the maximum similarity with the input signal.

The measure of similarity may be for example the correlation or the cross-correlation or another technique which maximises linearity between the synthetic signal and the input signal.

Thus with the present invention the candidates for the periodic signal which are effectively chosen in the frequency domain are used to generate a synthetic signal such as a pure sinusoid of the same frequency and this synthetic signal is compared in the time domain with the input signal. Whichever time domain synthetic signal has the highest cross-correlation with the input signal is regarded as the best estimate of the dominant periodic signal within the input signal.

The frequency domain candidates can be generated by spectral analysis of the input signal, for example by auto-regressive modelling, or by Fourier transform or any standard spectral analysis technique.

Preferably where auto-regressive modelling is used, a plurality of auto-regressive models of different order are fitted to the input signal, for example models of order from 2-20, though the range of orders used depends on the circumstances. Preferably synthetic signals are generated for the dominant (i.e. largest magnitude) pole from each of the fitted auto-regressive models, though with successively greater processing requirements the synthetic signals can be generated for all poles within a certain allowed frequency range and/or with a magnitude greater than a certain threshold (i.e. representing a periodic component of greater than a certain strength), or for all poles in the model.

Rather than subjecting the input signal to spectral analysis, it is alternatively possible to generate the frequency domain candidates by selecting a plurality of different frequencies within a predetermined allowed frequency range for the periodic signal. These may be evenly spaced over the frequency range. For example if it is known that the allowed frequency range for the periodic signal is from 0.5 to 5 Hz, candidates could be every frequency over that range with a frequency resolution of 0.1 Hz. Synthetic signals at 0.5 Hz, 0.6 Hz, 0.7 Hz . . . 4.8 Hz, 4.9 Hz, 5 Hz would thus be generated for use in the time domain similarity measurement, e.g. cross-correlation, step.

Preferably the input signal is temporally windowed, the window length being selected based on the particular application and the variability of the signal (for example into windows from 5 to 60 seconds long) and the steps of calculating the similarity and outputting a frequency estimate are performed for each window. The windows may be overlapping, for example with an overlap from 0.5 to 10 seconds, or spaced apart, for example by 1 to 10 seconds.

The input signal can be the noisy signal itself, or it can be subject to pre-processing before the generation of frequency domain candidates and similarity measurement. The pre-processing could involve detrending and/or filtering and/or re-sampling.

The step of calculating the cross-correlation of each synthetic signal with the input signal results in the output of a correlation coefficient. Preferably a threshold is placed on the similarity, e.g. the correlation coefficient, and a frequency estimate would only be output if the similarity for the synthetic signal of that frequency is above the threshold.

The invention is applicable to any noisy signal where the desire is to detect a single dominant periodic component. One example of such a noisy signal is a signal from a physiological sensor such as a PPG signal or a PPGi signal from a video camera. Thus the periodic component to be detected can be the heart rate or breathing rate.

Thus the input signal can be a time series of image intensity data such as a PPGi signal and it can comprise several colour channels, for example the conventional red, green and blue video channels, with each channel being processed separately.

The invention may be embodied in a computer program comprising program code means for executing on a computer system the method steps. Alternatively it can be embodied in firmware or hardware.

Another aspect of the invention provides an apparatus for analysing an input signal to estimate the frequency of a periodic signal therein, the apparatus comprising an input for receiving the input signal, a processor for processing the input signal, wherein the processor is configured to execute the method above. The apparatus further includes an output to output the frequency estimate, for example by means of a display.

The invention will be further described by way of example with reference to the accompany drawings in which:—

Figure 1:
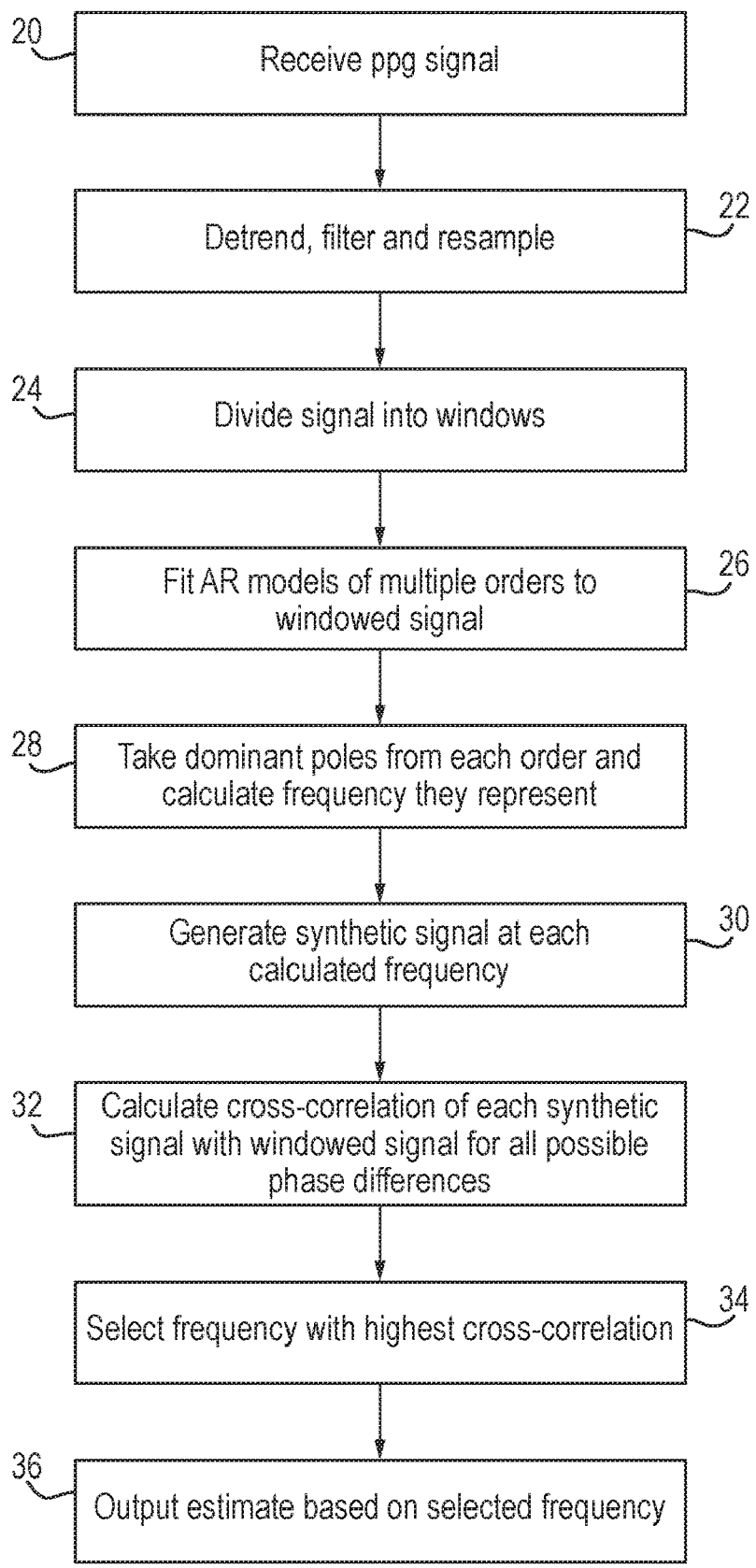
FIG. 1 is a flow diagram illustrating the method of one embodiment of the invention.

FIG. 1 is a flow diagram showing the application of an embodiment of the invention to the analysis of a PPG signal. In step 20 a PPG signal, which is the pulsatile waveform produced by a pulse oximeter at one of its two wavelengths (red and infra-red) is received. In step 22 this signal is detrended (e.g. by subtracting the mean or a linear fit over the whole signal) and filtered using a low-pass filter (Kaiser window, $f_{pass}$=0.5*cardiac frequency in Hz, $f_{stop}$=1.2*cardiac frequency). The signal is resampled, for example at a frequency of 5 Hz. This resampling is required in this embodiment because the intention is to find the respiration rate. The PPG signal itself has a high sampling rate of 100-250 Hz to ensure that the shape and heart rate information are preserved. However at such high sample rates the phase angles corresponding to breathing frequencies are very small and the cardiac-synchronous pulsatile component of the PPG signal (heart beat) is dominant. Downsampling ensures that the cardiac-synchronous pulsatile component is no longer dominant.

In step 24 the signal is divided into consecutive 32-second windows, each separated by 3 seconds. Longer or shorter windows can be used, and rather than being separated, the windows can overlap.

In step 26 multiple auto-regressive models with model orders ranging from 2-20 are applied to the windowed signal. In step 28 for each AR model the dominant pole, that it is to say the pole with the highest magnitude is identified. Thus 19 dominant poles, one from each of the model orders, is produced. Although in this embodiment only the dominant pole is taken from each model, it is possible alternatively to take all poles within a certain allowed frequency range, or to take all poles of each model onto the next step. Clearly taking more poles means a greater amount of processing.

In step 30, for each of the selected poles (in this example the nineteen dominant poles, one from each model order) a synthetic signal which is a pure sinusoidal signal at the frequency represented by the pole's phase angle and whose amplitude is determined by that of the signal that was modelled (for example by setting it equal to the standard deviation of the original signal) is generated. This sinusoid is therefore a time-domain representation of the dominant pole from each model. Then in step 32 the cross-correlation is calculated between each of the synthetic signals and the original modelled signal for all possible phase differences between the synthetic signal and the modelled signal. Each calculation will return a cross-correlation coefficient c. In step 34 whichever of the synthetic signals has the highest cross-correlation with the original signal is found (the maximum value of c) and in step 36 the frequency of this synthetic signal is output as the estimate of the strongest periodic component of the original input signal. In this example, analysing a downsampled PPG signal, the estimated respiration rate in breaths per minute can be obtained by taking the reciprocal of this frequency in Hertz and multiplying by 60.

Figure 2:
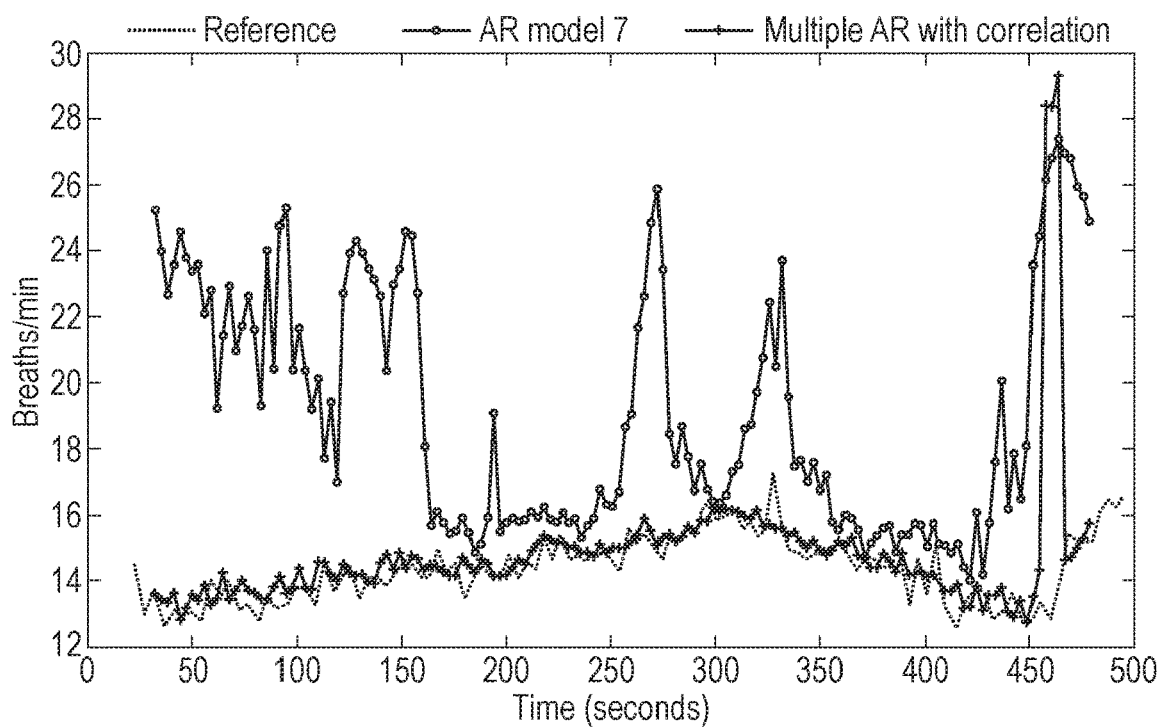
FIG. 2 shows the results of applying the embodiment of FIG. 1 to respiratory rate estimation and comparing it with other techniques for a patient with spontaneous breathing.
Figure 3:
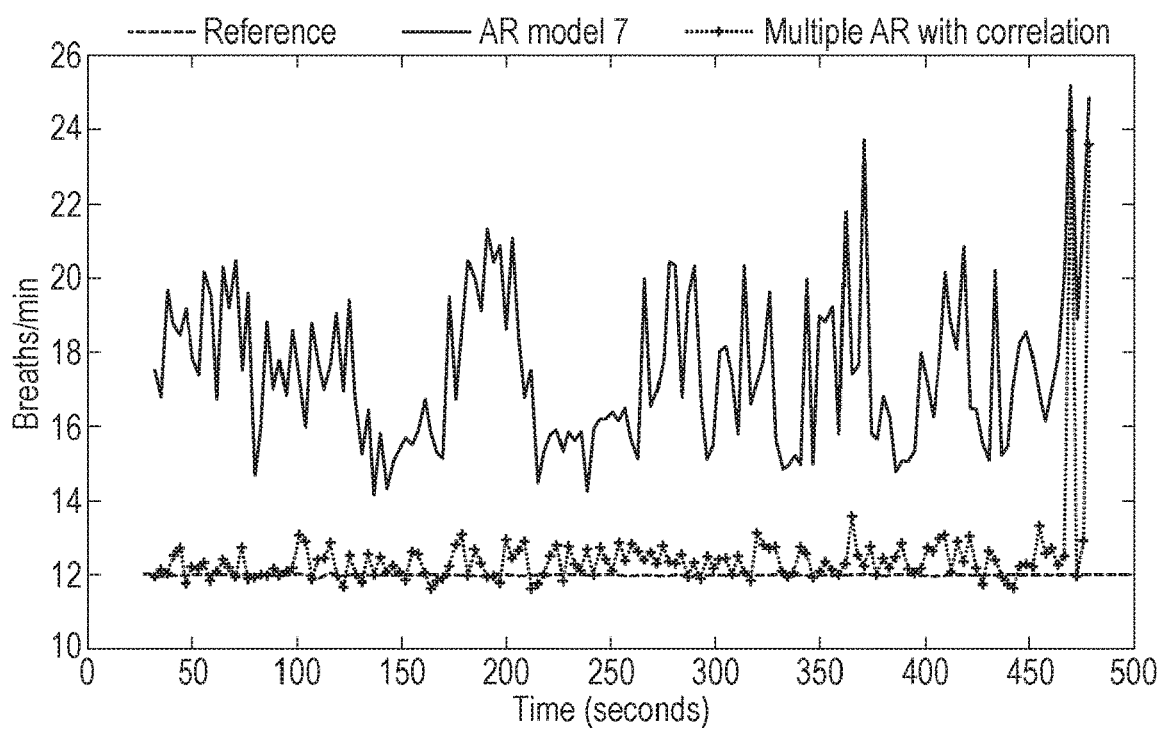
FIG. 3 shows the results of applying the embodiment of FIG. 1 to respiratory rate estimation and comparing it with other techniques for a patient with controlled breathing.

FIG. 2 illustrates the results of applying this example of the invention to a PPG recording in comparison with capnometry data as a reference and the auto-regressive modelling technique described in WO-A2-2013/027027. The capnometry reference measurements are shown in dotted, the results of applying the embodiment of the invention are shown in a thin line with ticks, and the results of the prior art auto-regressive modelling technique are shown in a thick line with dots. FIG. 2 is for a patient with spontaneous breathing whereas FIG. 3 shows results for a patient with controlled breathing (in FIG. 3 the reference is shown dashed, the prior art AR model in a solid line, and the embodiment of the invention in a dotted line with crosses). As can be seen the method of this embodiment of the invention tracks the breathing rate much more accurately than the prior art auto-regressive modelling method.

A specific example of the invention for application to analysis of a PPG signal has been described above. The invention is application, however, to any noisy time series of data where one is seeking a single periodic signal in the time series.

Thus more generally a given input time-series I(x) may is modelled by:

$$I(x) = \mu(I(x)) + \Sigma_j a_j \cos(\omega_j + \varphi_j) + \epsilon(x)$$

Where $\mu(I(x))$ is the average offset or trend, $\epsilon(x)$ is a random error associated with each data-point, and $\Sigma_j(a_j \cos(\omega_j x + \varphi_j))$ defines the Fourier series that describes the signal.

Assuming that this signal has a suspected dominant frequency $\Omega$ in a particular frequency range, it is detrended to obtain:

$$I'(x) = \text{detrend}\{I(x)\} = \Sigma a_j \cos(\omega_j x + \varphi_j) + \epsilon(x)$$

and finally filtered so as to be modelled by:

$$O(x) = \text{filter}\{I'(x)\} = A \cos(\Omega x + \Phi) + \epsilon(x)$$

For any given set of frequencies $\omega_k = \{\omega_1, \ldots, \omega_n\} = \{2\pi f_1, \ldots, 2\pi f_n\}$ that are thought to best approximate $\Omega$, a synthetic sinusoidal signal is generated for each frequency $S_k(x)$, such that the generated signal is $$S_k(x) = \cos(\omega_k x + \lambda)$$

This signal is cross-correlated with the original detrended and filtered signal $$O(x) \text{ over the lag} -\frac{1}{2f_k} < \lambda \le \frac{1}{2f_k}$$

$$R_k(\lambda) = (O(x) * S_k(x))[\lambda]$$

The frequency $\omega_k$ found to maximise the absolute value of $R_k$ is then selected as the best approximation of the dominant signal frequency $\Omega$, i.e. find $\omega_k$ that satisfies $$\text{argmax}\{(O * S_k)[\lambda]\}, \forall k$$

Standard methods of cross-correlation calculation may be used to evaluate $R_k$. Usually one may express $R_k$ as:

$$R_k(\lambda) = \Sigma_x (O[x] - \overline{O}) \cdot (S[x - \lambda] - \overline{S})$$

Alternatively, a more computational efficient model is to use the convolution theorem, i.e. that:

$$F\{f * g\} = (F\{f\})^* \cdot F\{g\}$$

where F denotes the Fourier Transform and * denotes the complex conjugate operand.

We may then write the cross correlation of the original signal with the synthetic signal as:

$$R = (\lambda) = (O(x) * S_k(x))[\lambda] = F^{-1}\{(F\{O\})^* \cdot F\{S\}\}$$

Finally, the relative amplitudes of the two signals need to be accounted for. This can be done in a number of ways:

i) Take this into account when generating the synthetic signal, i.e. by setting $$S_k(x) = B(x) \cos(\omega_k x + \lambda)$$

where B(x) matches the signal envelope. In its simplest form, $$B(x) = \text{std}(O(x))$$

ii) Normalise when cross-correlating, i.e. through:

$$R_k(\lambda) = \frac{F^{-1}\{(F\{O\})^* \cdot F\{S\}\}}{\sqrt{(0*0)[0](S*S)[0]}}$$

or simply through:

$$R_k(\lambda) = \frac{F^{-1}\{(F\{O\})^* \cdot F\{S\}\}}{\text{std}(O(x))\text{std}(S(x))}$$

In the above examples the candidates for the periodic component of the input signal are selected using auto-regressive modelling. However it is possible to generate these candidates in other ways. For example, instead of auto-regressive modelling another spectral analysis technique can be used to identify candidate spectral components. For example peaks in the Fourier transform spectrum or a wavelet transform method may be used. Alternatively, if the allowed frequency range for the signal of interest is relatively small, it is possible to generate "all" frequencies in that range (with a certain resolution separating them) and to generate synthetic signals corresponding to each of those frequencies.

Also in the above example cross-correlation is used as the time domain validation technique but other validation techniques in the time domain can be used. For example calculating the correlation or any other method that maximises the linearity between the synthetic signal and the input signal.

Figure 4:
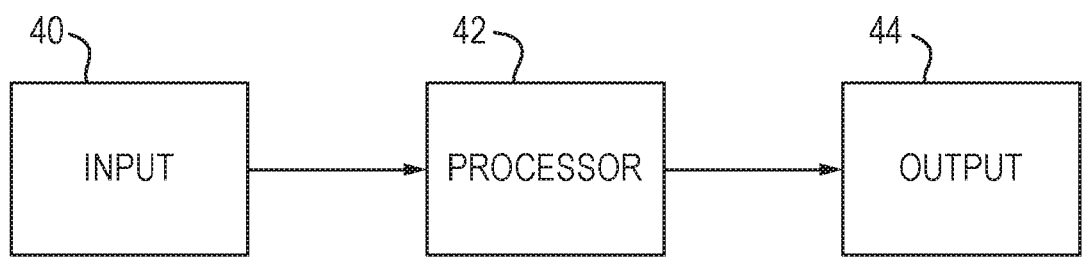
FIG. 4 schematically illustrates signal processing apparatus according to an embodiment of the invention.

The invention may be embodied as a computer program for running on a computer system which receives the input time series and outputs an estimate of the dominant periodic component within the time series. Alternatively the invention may be incorporated into a dedicated apparatus, such as a monitor, as schematically illustrated in FIG. 4. Such apparatus comprises an input 40 for receiving the input data, a process 42 for executing the data processing steps described above and an output 44, such as a display, for outputting the estimate of the dominant periodic component, for example as a physiological measurement such as a breathing rate or heart rate.

The invention claimed is:

1. A method of analyzing an input signal to estimate the frequency of a periodic signal therein comprising:
   receiving the input signal;
   generating frequency domain candidates for the periodic signal by performing spectral analysis on the input signal to detect spectral components of the input signal, the detected spectral components constituting the frequency domain candidates;
   for each frequency domain candidate generating a synthetic signal of the same frequency;
   calculating in time domain a measure of the similarity of each synthetic signal with the input signal;
   defining a similarity threshold;
   outputting as the estimate of the frequency of the periodic signal the frequency of the synthetic signal with maximum similarity with the input signal; and
   inhibiting the outputting if the similarity of the synthetic signal with the maximum similarity with the input signal is below the similarity threshold.

2. A method according to claim 1 wherein the measure of similarity is correlation or cross-correlation.

3. A method according to claim 1 wherein the spectral analysis is by autoregressive modelling.

4. A method according to claim 3 wherein a plurality of autoregressive models of different orders are fitted to the input signal.

5. A method according to claim 4 wherein the plurality of autoregressive models comprise models of order 2 to 20.

6. A method according to claim 3 wherein synthetic signals are generated for each pole in the fitted autoregressive models.

7. A method according to claim 3 wherein synthetic signals are generated for only poles in the fitted autoregressive models which correspond to a predetermined allowed frequency range for the periodic signal.

8. A method according to claim 3 wherein synthetic signals are generated for only poles in the fitted autoregressive models which have a predetermined magnitude.

9. A method according to claim 3 wherein synthetic signals are generated for only the dominant poles in the fitted autoregressive models.

10. A method according to claim 1 wherein the frequency domain candidates are generated by selecting a plurality of different frequencies within a predetermined frequency range.

11. A method according to claim 10 wherein the plurality of different frequencies are evenly spaced from each other over the frequency range.

12. A method according to claim 1 wherein the input signal is temporally windowed, for example from 5 to 60 seconds long, and the steps of calculating the similarity and outputting a frequency estimate are performed for each window.

13. A method according to claim 12 wherein the windows are overlapping windows, for example with an overlap from 0.5 to 10 seconds.

14. A method according to claim 1, wherein the input signal is obtained by de-trending and filtering a noisy signal.

15. A method according to claim 14 wherein the input signal is obtained by resampling the de-trended and filtered noisy signal.

16. A method according to claim 1, wherein the synthetic signal is sinusoidal.

17. A method according to claim 1, wherein the input signal is a time series of image intensity data.

18. A method according to claim 1 wherein the input signal is video image data comprising a time series of intensity data for each color channel.

19. A method according to claim 1 wherein the input signal is a measurement of a physiological parameter of a human or animal subject.

20. A method according to claim 19 wherein the periodic signal is the heart rate or respiration rate of the subject.

21. A computer program comprising program code means for executing on a computer system the method of claim 1.

22. Apparatus for analyzing an input signal to estimate the frequency of a periodic signal therein comprising:
an input for receiving the input signal;
a processor for processing input signal;
the processor being configured to execute the steps of claim 1; the apparatus further comprising an output to output as the frequency estimate the frequency of the synthetic signal with the maximum cross-correlation with the input signal.

* * * * *